United States Patent [19]

Teichner et al.

[11] 4,053,212
[45] Oct. 11, 1977

[54] TEST DISK FOR EYE EXAMINATION

[75] Inventors: Otwald Teichner, Wolfratshausen; Manfred Born, Munich, both of Germany

[73] Assignee: Optische Werke G. Rodenstock, Germany

[21] Appl. No.: 623,473

[22] Filed: Oct. 17, 1975

[30] Foreign Application Priority Data

Oct. 31, 1974 Germany .............................. 2451750

[51] Int. Cl.$^2$ .............................................. A61B 3/02
[52] U.S. Cl. .................................... 351/32; 351/13; 351/30; 351/36
[58] Field of Search ................. 351/13, 16, 30, 32, 351/36, 37, 6, 11; 352/72, 73; 354/175

[56] References Cited

U.S. PATENT DOCUMENTS

| 1,698,013 | 1/1929 | DeZeng | 351/32 X |
| 2,357,593 | 9/1944 | Leavell | 351/13 X |
| 3,486,813 | 12/1969 | Johnston | 351/56 X |
| 3,807,839 | 4/1975 | Sugarman et al. | 351/32 |
| 3,910,690 | 10/1975 | Regan | 351/36 |

*Primary Examiner*—Saxfield Chatmon, Jr.
*Attorney, Agent, or Firm*—Craig & Antonelli

[57] ABSTRACT

An exchangeable device providing test patterns for eye examinations is provided to be insertable into an eye examination instrument, such as a projector or an eyepiece instrument. This device includes a cassette containing a rotatable disk carrying different test patterns with the test patterns being visible through light transparent portions of the cassette. The cassette is insertable into the instrument, and the test pattern is illuminated through the light transparent portions with the disk being rotated through coupling elements connected to a drive mechanism of the instrument to vary the test pattern.

10 Claims, 4 Drawing Figures

TEST DISK FOR EYE EXAMINATION

This invention relates to a test disc having the shape of a circular disk with a number of test patterns to be displayed arranged in the peripheral zone of the disk and being capable of being transilluminated and/or projected. More particularly, this test disk is exchangeably insertable in ophthalmological examination devices, such as projectors or eyepiece instruments, and is arranged therein to be rotatable about an axis.

It is known in eye test projectors intended for a relatively small number of test patterns to fixedly mount rotatable, circular test disks within the housing, so that the disks are sufficiently protected from contact and contamination.

On the other hand, it is helpful to use, in visual symbol projectors and eye test instruments intended for direct viewing, circular test disks which can be exchangeably inserted in the device. In this type of instrument, it is possible to employ a variety of different test patterns, but the test disks are greatly soiled by dust and contact and exposed to direct damage. This has a very disadvantageous effect particularly in case of fine-structured test patterns.

It is an object of the invention to provide an exchangeable test disk for eye examination devices which is substantially free from contamination and damage to the test patterns.

This object is attaned in accordance with this invention by arranging the test disk in a tightly closed cassette which can be inserted, together with the test disk, into the eye examination instrument or projector. The cassette is clearly transparent at an observation position of the test patterns, and comprises coupling elements connected to the test disk for rotating the latter.

Test disks constructed in accordance with this invention can be exchanged in the eye examination instrument without effort and with great speed, while sensitive test patterns cannot be damaged or contaminated, on the other hand, by contact or the like.

In order to operate the test disk within its cassette, a disk shaft or axle may extend out of the cassette on at least one side, and is provided with coupling elements which engage drive elements of a driving mechanism for an eye examination instrument when the cassette has been inserted in the latter.

In order to start the rotary motion of the test disk at a certain rotational position with respect to the cassette and the examination instrument, the coupling elements can be fashioned so that the cassette can be inserted in the instrument only at a specific position of the test disk, wherein this specific test disk position can be fixed by a detent means. On the other hand, the cassette can be inserted into the eye examination instrument in any rotary position of the test disk, but in this connection the coupling elements and parts transmitting the rotary motion are resiliently constructed so that they only engage the drive elements of the eye examination instrument at certain predetermined positions of the test disk, when these drive elements begin their rotation. This resilient element can be, for example, a pin having a spring action in the axial or radial direction of the test disk, which pin can lock into a slot of the drive elements of the eye examination instrument at an appropriate rotary position. A large number of other mechanical arrangements can be utilized herein.

The test disks can be controlled in a conventional manner by a coding device rotating with the test disk in fixed correlation with the individual test patterns and being scanned electrically or photoelectrically. The concomitantly rotating coding means can be affixed to the test disk proper, or it can be connected to the drive elements in the eye examination instrument.

For the photoelectrical scanning of a coding means disposed directly on the test disk, the cassette can be provided at corresponding locations with light-permeable, but dustproof zones.

A coding device which can be scanned by electric sliding contacts can rotate on the outside of the cassette, together with the rotation of the test disk.

Within either the cassette or the mechanism of the drive elements of the eye examination instrument, a mechanical, resilient detent means can be provided which arrests the individual test patterns of the test disk at the observation site. Such a detent means can also be assoicated merely with the position of the test disk upon the insertion of the cassette in the eye examination instrument.

The drawing figures show one embodiment of this invention, to wit:

Figure 1:
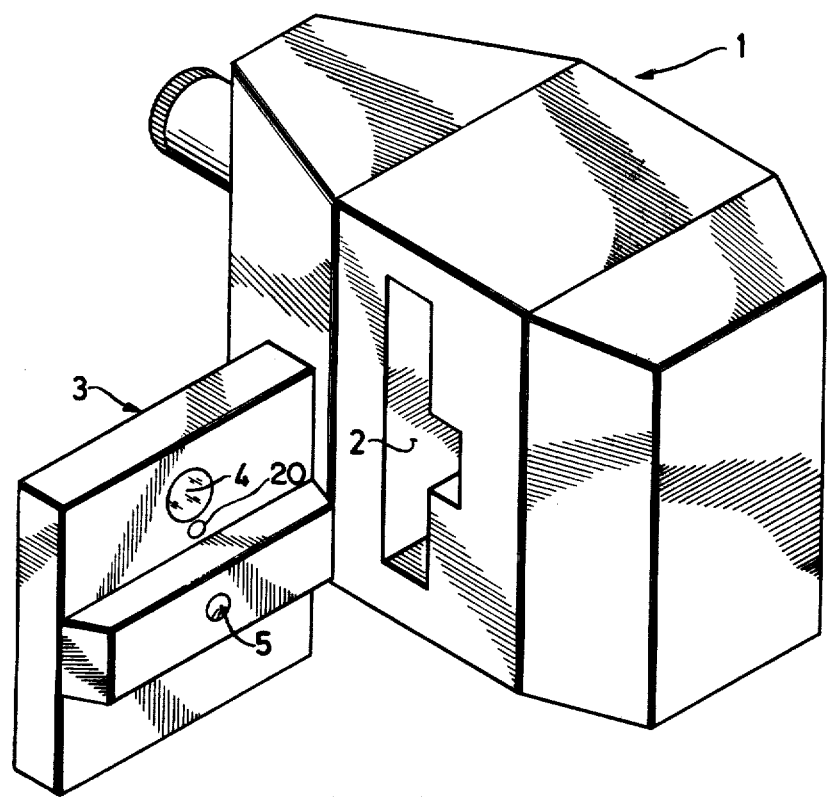
FIG. 1 shows a perspective view of a visual symbol projector with cassette.

In detail, FIG. 1 shows a visual symbol projector 1 having an insert aperture 2 which receives the cassette 3. The cassette 3 has a clear transparent zone 4 on opposite sides; and the individual test patterns of the test disk disposed within the cassette can be moved past this zone for observation or projection by the instrument 1. The test disk moves about a shaft or axle 5. A second clear transparent zone 20 may be included on opposite sides of the cassette 3 for decoding purposes.

Figure 2:
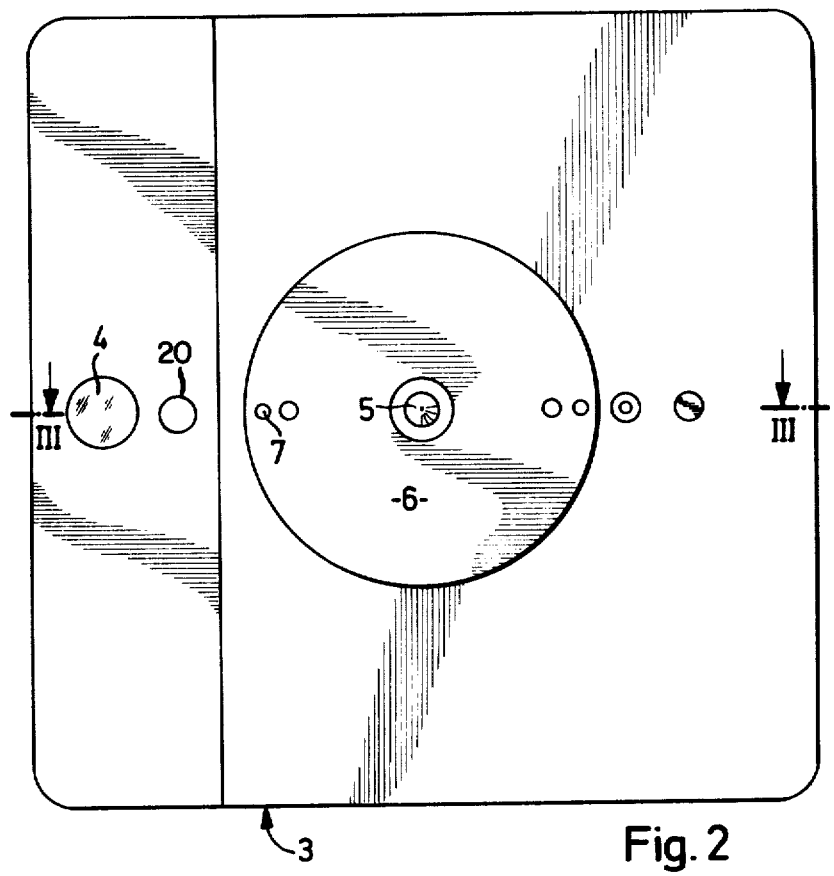
FIG. 2 is an axial view of a cassette.

FIG. 2 shows the cassette 3 as seen in the direction of the axle 5. A plate or disk 6 connected to the axle 5 carries coupling elements or pins 7 intended for ensuring that the test disk 8 is in a predetermined position when the cassette 3 is inserted into the visual symbol projector 1.

Figure 3:
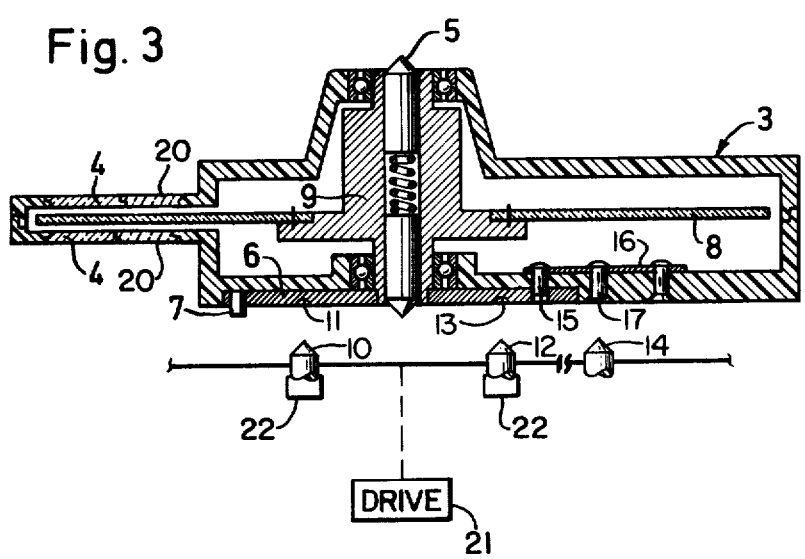
FIG. 3 is a cross section through the cassette of FIG. 2 along the line III—III.

The sectional view of the cassette 3 in FIG. 3 shows the test disk 8 connected via the hub 9 with the disk 6 and the coupling elements or pins 10, 12 of the drive mechanism (not shown) for engaging the bores 11, 13 respectively, of the disk 6 for rotation thereof. The hub 9 is rotatably mounted on the axle 5, which latter is constructed to be resilient in the axial direction by means of a spring. Either the coupling elements 7 or the drive elements 10, 12 of the projector 1 may have an axially or radially resilient member to be locked into corresponding recesses or cut-outs of the drive elements or coupling element, such as bores 11, 13, respectively to effect a positive driving coupling for driving the disk 6. Elements 22 are resilient members used to resiliently couple pins 10, 12 with the disk 6.

Thus, in the embodiment of FIG. 3 the disk 6 is driven by way of pins 10, 12 engaging corresponding bores 11, 13 in the disk 6. The pin 7 present in the disk 6 ensures that the cassette can be inserted in the device only if the test disk 8 is in the basic position. A rotation of the test disk 8 with the cassette being removed is prevented by a retaining spring 16 to which is attached a pin 15 engaging the disk 6. When the cassette is disposed in the device, the leaf spring 16 is lifted by a resilient, conically extending pin 14 so that the engaging pin 15 is released, allowing rotation of the disk 6. Elements 14–16 may also be utilized as a positive detent mechanism. The test disk 8 is accordingly driven via a positive drive connection from a drive mechanism (not shown) such as a conventional drive motor.

The test disk 8 may be in the form of a circular disk having a plurality of individual test patterns arranged along the periphery of the disk 8. Illumination sources of the projector 1 illuminate and project an image of a corresponding test pattern which may appear in the transparent zone 4. The various test patterns are changed by rotation of the circular disk 8 about the shaft 5, as above, by the driving mechanism (not shown) of the instrument 1. A detent may be provided between the disk 8 and cassette 3 to correspond to one or more rotary positions of the disk.

A further feature of the cassette 3 resides in that a portion of the shaft 5 and/or return hub 9 may extend out of the cassette with a structure cooperating with an associated portion of the projector 1, so that a specific starting position of the test disk 8 is attained with respect to the drive elements of the projector 1 when the cassette is inserted in the instrument.

Figure 4:
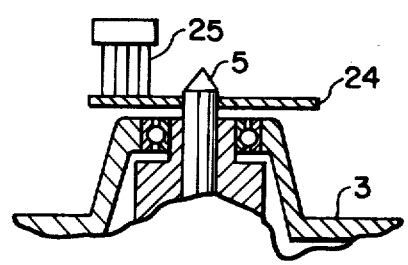
FIG. 4 is a partial view of the cassette of FIG. 3 modified according to an additional embodiment of the present invention to provide an additional coding disk.

For controlling the position of the test disk 8 for a selected test pattern, a coding mechanism may be utilized in which various coded zones correspond to associated test patterns. This coding mechanism may be included with the test disk for rotation therewith, and a read-out and control mechanism is provided responsive to the coded zones. In one arrangement, the coding mechanism may be directly associated with the test disk and transparent portions are provided in the cassette for photoelectric scanning of the coded zones. In another arrangement, the coding mechanism is provided at the exterior of the cassette for scanning of the coded zones by electric sliding contacts. In the latter case, the coding mechanism is connected to be rotatable with the test disk 8. FIG. 4 illustrates this alternative embodiment. Transparent zones 20 are not present and shaft 5 has been extended to accommodate the encoder wheel 24 designed to engage contacts 25.

While we have shown and described one embodiment in accordance with the present invention, it is understood that the same is not limited thereto but is susceptible of numerous changes and modifications as known to a person skilled in the art, and we therefor do not wish to be limited to the details shown and described herein but intend to cover all such changes and modifications as are obvious to one of ordinary skill in the art.

We claim:

1. An exchangeable test pattern device for ophthalmological examination instruments comprising
   a cassette housing for insertion into an ophthalmological examination instrument, said cassette housing including at least one transparent portion,
   a disk rotatably mounted in said cassette housing, said disk including a plurality of test patterns, each of said test patterns being selectively visible at said transparent portion, and
   means for rotating said disk.

2. A device according to claim 1, wherein said cassette housing is tightly closed.

3. A device according to claim 1, wherein said plurality of test patterns are arranged in a peripheral zone of said disk.

4. A device according to claim 1, wherein said disk is circular.

5. A device according to claim 1, wherein said means for rotating includes shaft means for rotatably supporting said disk, said shaft means having a portion extending out of at least one side of said cassette housing and coupling means operatively connected to said shaft means for coupling with drive means of said ophthalmological examination instrument.

6. A device according to claim 5, wherein said portion of said shaft means includes means cooperating with an associated portion of said ophthalmological examination device for attaining a predetermined starting position of said rotatable disk.

7. A device according to claim 6, wherein at least one of said coupling means and said drive means include one of an axially resilient member and a radially resilient member for lockingly engaging a corresponding recess of the respective one of said drive means and said coupling means, such that a driving coupling is effected between saud coupling means and said drive means.

8. A device according to claim 1, wherein detent means are provided between said cassette housing and said rotatable disk for holding said disk in at least one rotary position.

9. A device according to claim 1, wherein coding means associated with said test patterns is arranged on said disk for detecting said test patterns, said cassette housing including at least one further transparent portion corresponding to said coding means, said coding means being photoelectrically scanned through said further transparent portion.

10. A device according to claim 1, wherein coding means associated with said test patterns is provided on an exterior portion of said cassette housing for detacting said test patterns, said coding means being connected for rotation with said rotatable disk, and said coding means being scanned by electric sliding contacts.

* * * * *